United States Patent [19]
Higashi

[11] Patent Number: 5,929,442
[45] Date of Patent: Jul. 27, 1999

[54] APPARATUS FOR AND METHOD OF ANALYZING CARBON ISOTOPES

[75] Inventor: Yoji Higashi, Higashiyamato, Japan

[73] Assignee: Japan Radio Co., Ltd., Tokyo, Japan

[21] Appl. No.: 08/827,408

[22] Filed: Mar. 27, 1997

[30] Foreign Application Priority Data

May 1, 1996 [JP] Japan ................................. 8-110993

[51] Int. Cl.[6] ................................................. G01N 21/35
[52] U.S. Cl. ..................................................... 250/339.13
[58] Field of Search ........................................ 250/339.13

[56] References Cited

U.S. PATENT DOCUMENTS

| | | | |
|---|---|---|---|
| 5,026,991 | 6/1991 | Goldstein et al. | 250/343 |
| 5,173,749 | 12/1992 | Tell et al. | |
| 5,459,574 | 10/1995 | Lee et al. | |
| 5,543,621 | 8/1996 | Sauke et al. | 250/339.03 |
| 5,703,365 | 12/1997 | Ishihara et al. | 250/339.13 |
| 5,747,807 | 5/1998 | Atkinson et al. | 250/339.13 |

OTHER PUBLICATIONS

G. Talsky and L. Mayring, "Über die analoge on–line–Differentiation höherer Ordnung zur . . ." *Fresenius Z. Anal. Chem.*, 292 (1978), pp. 233–235.

G. Talsky et al, "Feinauflösende UV/VIS–Derivativspektrophotometrie höherer Ordnung" *Angew. Chem.*, No., 90, 1978, pp. 840–854.

N. Hager, R. Stäudner, "Derivativ–Spektroskopie in der Gasanalyse" *Technisches Messen atm*, No. 11 (1976), pp. 331–335.

Yoji Higashi article entitled "Stable Isotope Analysis Using Tunable Diode Laser Spectoroscopy and its Application to [13]C–Breath Test" published in the Bulletin of the Society For The Medical Application of Carbon Thirteen, vol. 4, Oct., 1994, Title Page, and pp. 8, 9 and 52 and partial translation thereof.

"Table 1.2: Double Heterojunction Crystal And Laser Oscillation Wavelength", published in Semiconductor Laser And Applied Techniques, Kougakusha, Sep. 10, 1986, Title page, publication data page and p. 48 with translation of pertinent portions thereof.

"1.95–$\mu$m Strained InGaAs–InGaAsP–InP Distributed––Feedback Quantum–Well Lasers", by R.U. Martinelli, et al published in the IEEE Photonics Technology Letters, vol. 6. No. 12, Dec., 1994, pp. 1415–1417.

WPI Abstract Accession No. 94–037398 & JP 5340872 A (Japan Radio) Dec. 24, 1993.

*Primary Examiner*—Constantine Hannaher
*Attorney, Agent, or Firm*—Frishauf, Holtz, Goodman, Langer & Chick, P.C.

[57] ABSTRACT

The light absorption spectrum of carbon isotopes $^{12}CO_2$ and $^{13}CO_2$ is measured highly accurately within a short period of time to determine a carbon isotopic abundance ratio highly accurately and reliably. Laser light emitted from a laser diode, which has been slightly modulated with a frequency f and swept in wavelength, passes through a specimen cell and is applied to a photodetector, which produces an electric signal converted from the detected laser light. 2f components of $^{12}CO_2$ and $^{13}CO_2$ of the light absorption spectrum are detected by a lock-in amplifier, and 3f components of $^{12}CO_2$ and $^{13}CO_2$ of the light absorption spectrum are detected by a lock-in amplifier. Spectral intensities of $^{12}CO_2$ and $^{13}CO_2$, which correspond to zero-cross points of the 3f components, are determined from peak values at three points of each of the 2f components, and a carbon isotopic abundance ratio of $^{12}CO_2$ and $^{13}CO_2$ is determined from a ratio of the spectral intensities.

15 Claims, 7 Drawing Sheets

APPARATUS FOR AND METHOD OF ANALYZING CARBON ISOTOPES

BACKGROUND OF THE INVENTION

1. Field of the Invention

The present invention relates to an apparatus for and a method of analyzing carbon isotopes to determine a carbon isotopic abundance ratio by applying light to a specimen of carbon dioxide ($CO_2$) and detecting the light absorption spectrum of the specimen.

2. Description of the Related Art

Carbon atoms include isotopes whose mass numbers are $11(^{11}C)$, $12(^{12}C)$, $13(^{13}C)$, and $14(^{14}C)$. The carbon isotopes $^{12}C$, $^{13}C$ are stable isotopes which are safe as they cause no radiation exposure unlike the radioactive carbon isotopes $^{11}C$, $^{14}C$. Therefore, research efforts are being made to utilize the carbon isotopes $^{12}C$, $^{13}C$ especially Ln the medical field.

Recently, much attention has been attracted among internists to the relationship between an intragastric infection caused by *helicobacter pylori* (HP) and a gastric ulcer. The $^{13}C$-urea breath test (UBT) has increasingly been used for the diagnosis of an infection caused by HP.

UBT needs to be accompanied by a stable carbon isotope analyzer. Since UBT is conducted clinically, the stable carbon isotope ratio analyzer should preferably be small in size, easily operable for a simple and quick analysis, highly reliable, and inexpensive.

Heretofore, a mass spectrometer (MS) and an infrared spectrometer (IR) are known for use as the stable carbon isotope analyzer. The MS is capable of producing highly accurate outputs, but is difficult to operate and highly expensive. The IR is simple and inexpensive, but low in output accuracy.

There have been proposed analyzers based on laser spectroscopy as new carbon isotope analyzers for solving the above problems. One such analyzer based on laser spectroscopy employs a semiconductor laser which produces a laser emission having a wavelength in a 1.6 μm band. See "Isotope analyzer based on laser spectroscopy and its application to $^{13}C$ expiration test (II)", $^{13}C$ Medicine, VOL. 4, pp. 8–9, 1994. This analyzer uses a laser diode (LD) of the DFB (distributed feedback) type which is made of an InGaAsP material belonging to the III–V group of the periodic table. The laser diode is capable of single-mode oscillation at normal temperature and is small in size and highly reliable. The laser diode has many practical advantages including easy wavelength sweeping through the control of the laser diode temperature and drive current. Use of the laser diode allows a simple and quick analysis.

However, since the light absorption spectrum of $CO_2$ has a small absorption intensity in the 1.6 μm band, it is necessary that $CO_2$ contained in a human exhalation (the concentration of $CO_2$ in a human exhalation is about 2 to 5%) be concentrated by a pretreatment device before being analyzed in order to increase the amount of light absorption by $CO_2$. Specifically, the pretreatment device (concentrates $CO_2$ by solidifying $CO_2$ contained in a human exhalation with liquid nitrogen, i.e., converting it into dry ice, and thereafter removing unwanted gases of $N_2$, $O_2$, etc. with a vacuum pump. Because of the pretreatment device needed to concentrate $CO_2$, the analyzer is necessarily large in size and expensive to manufacture. The running cost of the analyzer is also high as it requires liquid nitrogen to concentrate $CO_2$. Another problem is that the analyzer is limited to certain places in its usage as liquid nitrogen is available not at any arbitrary spots.

Since it is known that there exists a spectrum having a large light absorption intensity of $CO_2$ in the vicinity of wavelengths of 2.0 μm and 4.3 μm (it is necessary to select a spectrum having a large light absorption intensity of $^{13}CO_2$ because a naturally occurring ratio of C for an isotopic analysis is $^{13}C/^{12}C \approx 1/99$), the above shortcomings may be overcome by using this spectrum. However, the laser diode of InGaAsP belonging to the III–V group cannot be used in the above wavelength range because it does not continuously oscillate at room temperature in that wavelength range (see Table 1.2, Double-heterojunction crystal and laser oscillation wavelengths", Semiconductor laser and applied techniques, Kougakusha, P48).

A laser diode made of a lead salt material belonging to the IV—IV group oscillates in a frequency range from 4 to 30 μm, but does not continuously oscillate at normal temperature. Therefore, this laser diode needs a large-size freezer which uses liquid helium, liquid nitrogen, or the like for its continuous oscillation. The laser diode also needs to kept in a very low temperature of 4 K or 77 K by an expensive cryostat having a vacuum heat insulation structure. Accordingly, the entire apparatus is large in size, cannot be handled with ease, is highly expensive, and hence does not lend itself to usage at clinical locations.

Figure 6:
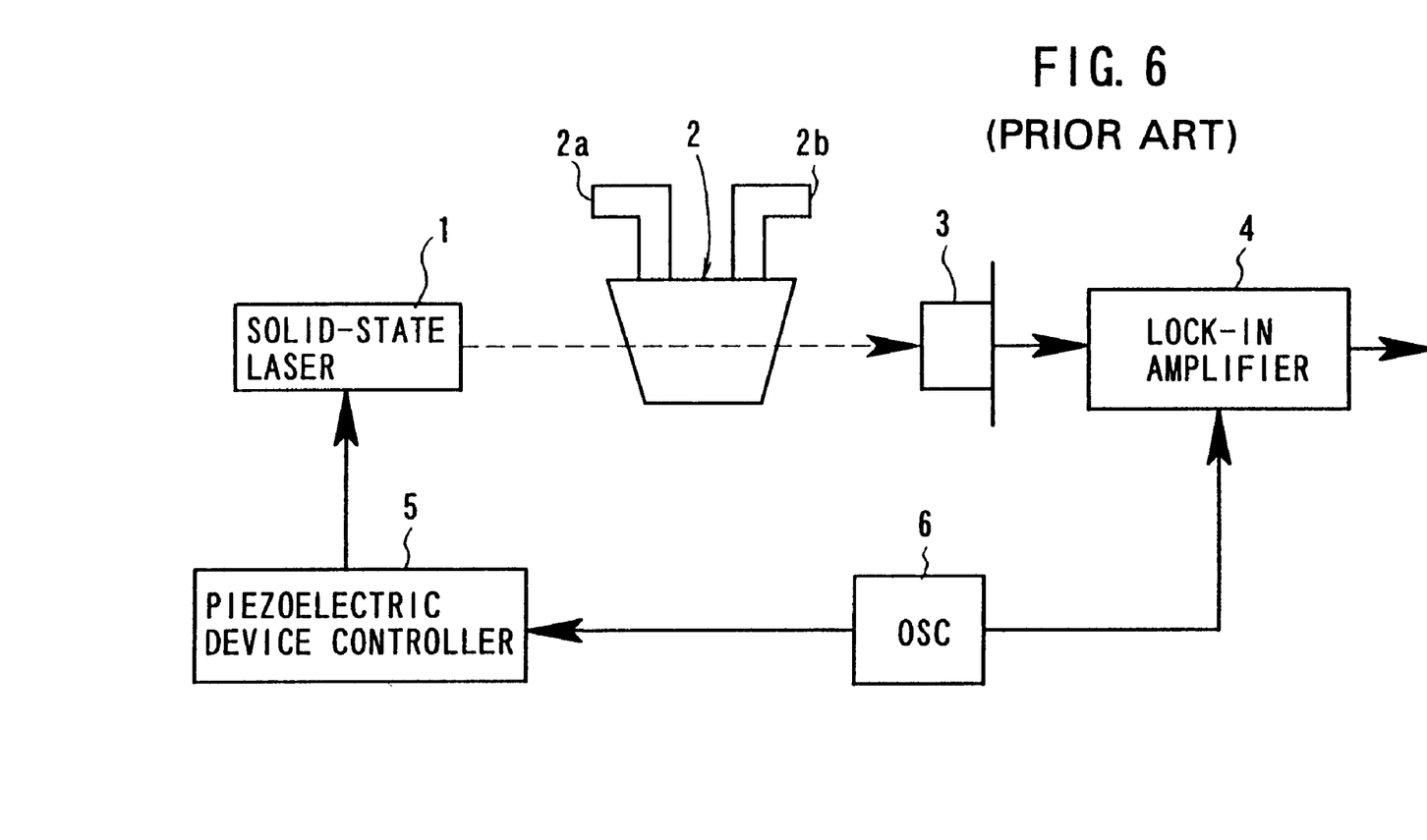
FIG. 6 is a block diagram of a conventional carbon isotope analyzer.

To solve the above problems, there has been proposed a carbon isotope analyzer which has a spectral laser source comprising an LD-pumped solid-state laser that oscillates in a single mode at normal temperature in a 2 μm band. FIG. 6 of the accompanying drawings shows the proposed carbon isotope analyzer. As shown in FIG. 6, the carbon isotope analyzer has an LD-pumped Tm:YAG solid-state laser 1, a specimen cell 2, a photodetector 3, a lock-in amplifier 4, a piezoelectric device controller 5 for controlling a piezoelectric device 12 (see FIG. 7 of the accompanying drawings), and an oscillator 6 for frequency-modulating oscillated light of the solid-state laser 1.

Figure 7:
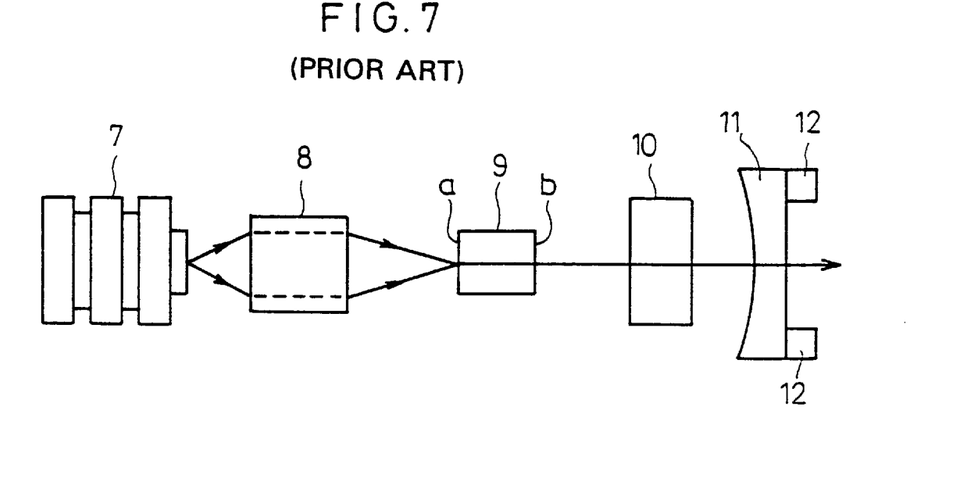
FIG. 7 is a schematic view of an LD-pumped solid-state laser in the conventional carbon isotope analyzer shown in FIG. 6.

The solid-state laser 1 is schematically shown in FIG. 7. As shown in FIG. 7, the solid-state laser 1 has a high-output laser diode 7, an optical system 8 which optically couples emitted light from the laser diode 7 to a laser resonator, and a Tm:YAG rod 9 having an end "a" facing the optical system 8 and an opposite end "b" facing a wavelength selector 10. The end "a" is coated with a layer which has a high transmittance with respect to exciting wavelengths and a high reflectance with respect to oscillated wavelengths, and the end "b" is coated with a layer which has a low reflectance with respect to oscillated wavelengths. The wavelength selector 10 comprises a combination of birefringent filters, etalon, or the like. The solid-state laser 1 also includes an output mirror 11 for the laser resonator, and the piezoelectric device 12 which is mounted on the output mirror 11.

The end "a" of the Tm:YAG rod 9 and the output mirror 11 jointly make up the laser resonator. Exciting light emitted from the high-output laser diode 7 is coupled by the optical system 8 to the Tm:YAG rod 9 to match an oscillation mode of the laser resonator. As a result, the Tm:YAG rod 9 is excited with high efficiency, causing the laser resonator to oscillate a laser beam which is outputted from the output mirror 11. The wavelength of the oscillated laser beam is selected to be any arbitrary wavelength in the vicinity of 2 μm by the wavelength selector 10 which is inserted in the laser resonator.

When a bias voltage and a modulation voltage are applied to the piezoelectric device 12 mounted on the output mirror 11, the length of the laser resonator is slightly varied to modulate the frequency of the oscillated laser beam.

The solid-state laser 1 is controlled by the wavelength selector 10 to cause its oscillated wavelength to sweep a range which covers the spectrums of both $^{13}CO_2$ and $^{12}CO_2$. A modulation signal from the oscillator 6 is amplified by the piezoelectric device controller 5, and applied, together with the bias voltage, to the piezoelectric device 12 of the solid-state laser 1. In this manner, the oscillation spectrum of the solid-state laser 1 is modulated.

The output laser light from the solid-state laser 1 which is thus frequency-modulated and wavelength-swept is introduced into the specimen cell 22. The specimen cell 2 contains a specimen, i.e., a $CO_2$ gas, which has been introduced from a specimen gas inlet 2a under a pressure sufficient enough to distinguish the fine structure of the light absorption spectrum of $CO_2$. The laser light which has entered the specimen cell 2 acts with the specimen, i.e., $CO_2$, in the specimen cell 2, causing a resonance absorption. The light which leaves the specimen cell 2 is detected by the photodetector 3, which applies an output signal to the lock-in amplifier 4 that detects only a signal synchronized with the frequency of the oscillator 6. As a result of such synchronous detection, the lock-in amplifier 4 can detect a signal of high S/N while removing fluctuations of the light output due to wavelength sweeping and noise inherent in the solid-state laser. The specimen gas is discharged from the specimen cell 2 from a specimen gas outlet 2b.

Figure 8:
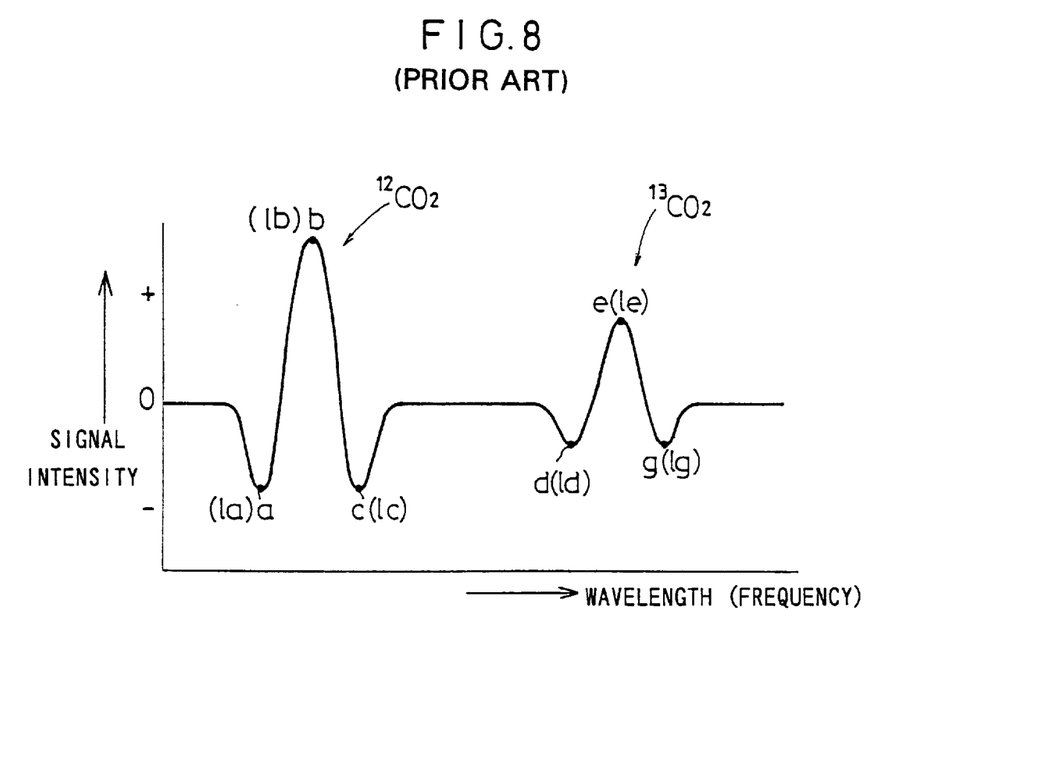
FIG. 8 is a diagram showing the waveform of a 2f spectrum of $^{12}CO_2$ and $^{13}CO_2$ produced by wavelength sweeping of the conventional carbon isotope analyzer shown in FIG. 6.

The signal from the photodetector 3 is detected by the lock-in amplifier 4 as a second derivative (2f spectrum) of the form of the light absorption spectrum (see FIG. 8 of the accompanying drawings). Peak values of the obtained light absorption spectrum signals of $^{12}CO_2$ and $^{13}CO_2$ are determined, and a ratio of the absorption intensities of $^{12}CO_2$ and $^{13}CO_2$ is determined from the peak values as an isotopic abundance ratio.

In the carbon isotope analyzer shown in FIG. 6, the spectrum in the vicinity of 2 μm where the light absorption intensity of $CO_2$ is high is measured through the lock-in amplifier 4, and the laser light is utilized substantially in its entirety. Therefore, the isotopic abundance ratio can be measured with high sensitivity. As a consequence, the pretreatment device, referred to above, may be dispensed with.

However, the carbon isotope analyzer shown in FIG. 6 is disadvantageous for the following reasons: The wavelength sweeping is carried out by controlling the wavelength selector 10 to produce the spectrum shown in FIG. 8 (with about 2000 samples in the direction of the wavelength sweeping). Since the wavelength selector 10 needs to be mechanically varied with ultrahigh precision for the wavelength sweeping, the wavelength sweeping is time-consuming and the time required for the analysis is quite long. If the time interval between the measurements of the spectrums of $^{12}CO_2$ and $^{13}CO_2$ is long, then the pressure of the specimen gas in the specimen cell 2 may vary due to a gas adsorption and a temperature change during that interval. This results in the measurement of a spectrum under a different pressure, and hence a reduced level of measurement accuracy. Furthermore, inasmuch as the wavelergth selector 10 is controlled with ultrahigh precision, it is susceptible to disturbances including oscillations, heat changes, etc., and low in reliability.

SUMMARY OF THE INVENTION

It is therefore an object of the present invention to provide an apparatus for and a method of analyzing carbon isotopes so as to be able to measure the light absorption spectrums of $^{12}CO_2$ and $^{13}CO_2$ highly accurately in a short period of time, and also to determine a high carbon isotopic abundance ratio highly accurately and reliably.

The above and other objects, features and advantages of the present invention will become more apparent: from the following description when taken in conjunction with the accompanying drawings in which preferred embodiments of the present invention are shown by way of illustrative example.

DETAILED DESCRIPTION OF THE PREFERRED EMBODIMENT

The context and principles of the present invention will briefly be described below.

Intensive research and development efforts have been made to develop near-infrared semiconductor laser diodes (LDs) made of an AlGaAsP or InGaAsP material belonging to the III–V group of the periodic table for use in optical communication and optical information processing fields, and near-infrared semiconductor laser diodes which are small in size and high in efficiency and reliability have been manufactured for practical use.

Such a laser diode continuously oscillates at normal temperature, and can readily be used a variable-wavelength light source when its temperature or drive current is controlled. Particularly when the drive current is controlled, the laser diode can dynamically vary the waveform, i.e., for wavelength sweeping.

If such a practically advantageous laser diode is incorporated in a carbon isotope analyzing apparatus, then the carbon isotope analyzing apparatus can be highly reduced in overall size for easy handling. Since the laser diode oscillates stably, the carbon isotope analyzing apparatus is highly reliable in use.

Heretofore, conventional laser diodes male of InGaAsP materials oscillate in a wavelength range up to 1.65 $\mu$m, and, as described above, it is necessary to concentrate $CO_2$ contained in a sampled human exhalation in order to detect a $CO_2$ spectrum with high accuracy. With recent advances in the laser diode fabrication technology, however, it has become possible to produce a laser diode of InCaAsP having a strain superlattice quantum-well structure which can oscillate continuously at normal temperature in a 2 $\mu$m band (see "1.95-$\mu$m Strained InGaAsP-InP Distributed--Feedback Quantum-Well Laser", IEEE PHOTONICS TECHNOLOGY LETTERS, Vol. 6, No. 12, December 1994, pp. 1415–1417).

According to the present invention, the third derivative waveforms (3f spectrums) of respective light absorption spectrums of $^{12}CO_2$ and $^{13}CO_2$ are determined using a laser diode which can oscillate continuously at normal temperature in a 2 $\mu$m band, and the oscillation wavelength of the laser diode is locked to the zero-cross points of the 3f spectrums as a wavelength discrimination curve. Three peak values of 2f spectrums of the light absorption spectrums of $^{12}CO_2$ and $^{13}CO_2$ are then determined to obtain light absorption intensities. In this manner, a carbon isotopic abundance ratio can be measured highly accurately in a short period of time, i.e., at a high speed. While such accurate and high-speed measurement of a carbon isotopic abundance ratio has not been possible with the conventional solid-state laser 1 shown in FIG. 6 because of the difficulty in dynamic control of the oscillation wavelength thereof, it has been made possible by the present invention through the use of such a laser diode in the 2 $\mu$m band.

Carbon isotope analyzing apparatus according to the present invention will be described below. Some of those parts of the carbon isotope analyzing apparatus according to the present invention which are identical to those of the conventional solid-state laser 1 shown in FIGS. 6 and 7 are denoted by identical reference numerals and letters. FIGS. 6 through 8 which are illustrative of the conventional solid-state laser 1 may also be referred to when necessary in the description of the present invention.

Figure 1:
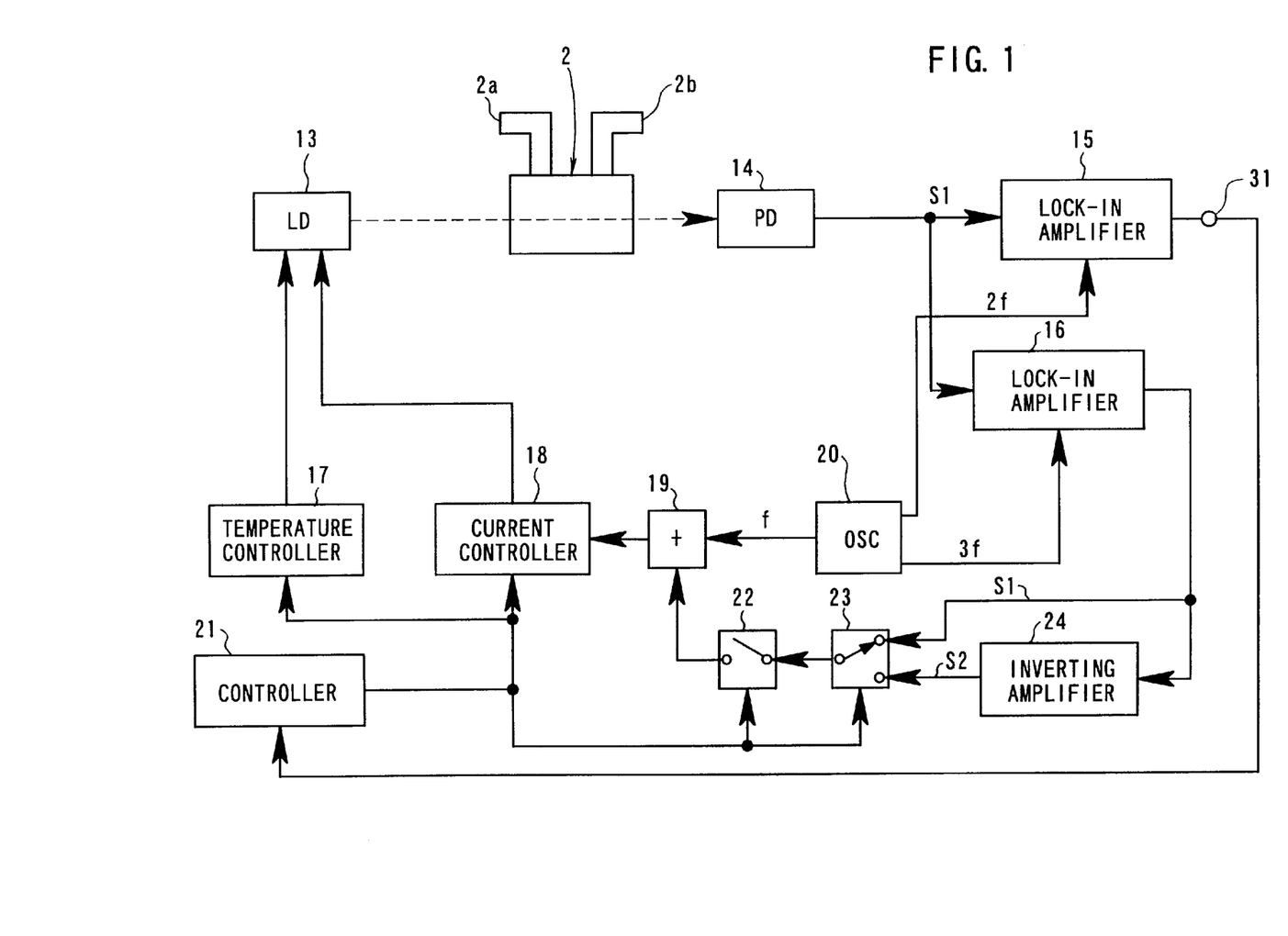
FIG. 1 is a block diagram of a carbon isotope analyzing apparatus according to an embodiment of the present invention.

FIG. 1 shows in block form a carbon isotopes analyzing apparatus according to an embodiment of the present invention. As shown in FIG. 1, the carbon isotope analyzing apparatus has a semiconductor laser diode (LD) 13, referred to above, which oscillates in a single mode in the 2 $\mu$m band, a specimen cell 2 having a specimen gas inlet 2a and a specimen gas outlet 2b, a photodetector 14, a pair of lock-in amplifiers 15, 16, a laser diode temperature controller 17, an laser diode current controller 18, and an oscillator 20 for frequency-modulating a drive current for the laser diode 13. The oscillator 20 outputs a signal having a fundamental frequency f, a signal having a frequency 2f which is twice the fundamental frequency f, and a signal having a frequency 3f which is three times the fundamental frequency f. The carbon isotope analyzing apparatus also has an adder 19, a controller 21 comprising microcomputer, an on/off switch 22, a selector switch (multiplexer) 23 for selecting one signal from two signals, and an inverting amplifier 24 for inverting the polarity of a signal applied thereto.

The microcomputer of the controller 21 functions as driving, controlling, processing, decision means, for example, and comprises a one-chip LSI device including a microprocessor (MPU), which corresponds to a central processing unit (CPU), A/D and D/A converters connected as input/output devices to the microprocessor, an I/O port, a read-only memory (ROM) which stores a control program, a system program, and look-up tables, a random-access memory (RAM: write/read memory) for temporarily storing processed data, a timer circuit, an interrupt processing circuit, and other circuits.

An exhalation of a person under test is introduced from the specimen gas inlet 2a into the specimen cell 2. The introduced exhalation is kept under a low pressure to prevent spectrums from being spread under excessive pressures.

Figure 2:
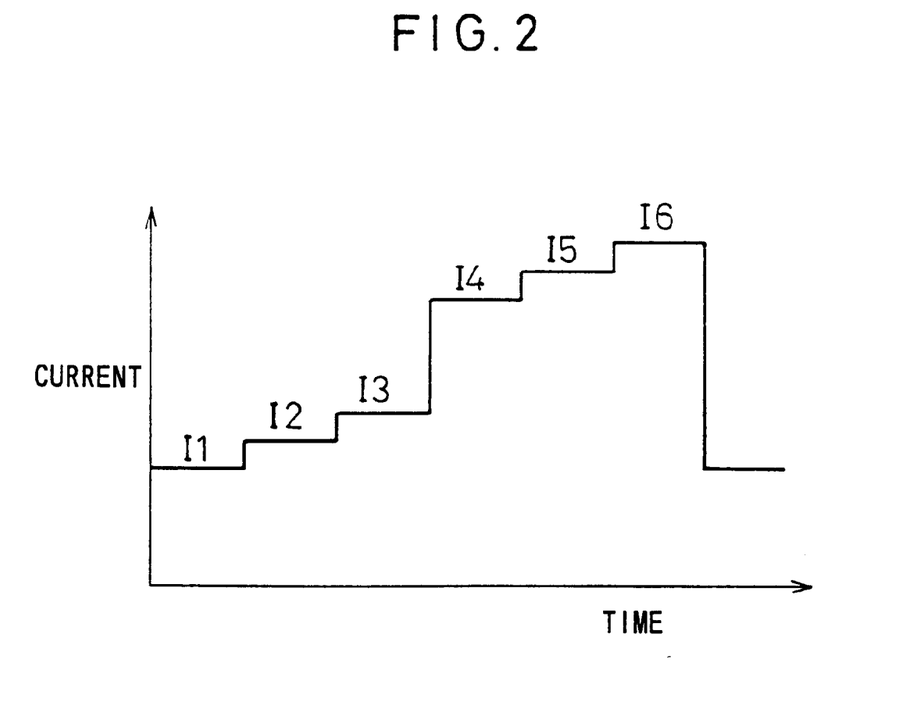
FIG. 2 is a diagram showing the waveform of a current control signal produced by a controller in the carbon isotope analyzing apparatus shown in FIG. 1.

The temperature of the laser diode 13 is controlled to establish a sweeping start wavelength (frequency) by the temperature controller 17 in accordance with a control signal from the controller 21. The laser diode 13 is supplied with a drive current from the current controller 18 in accordance with a control signal from the controller 21. The drive current supplied to the laser diode 13 has a stepwise shape having steps I1, I2, ..., I6, as shown in FIG. 2. The stepwise drive current causes this laser diode 13 to oscillate at wavelengths (frequencies) near points "a", "b", "c", "d", "e", "g" shown in FIG. 8.

Figure 3A:
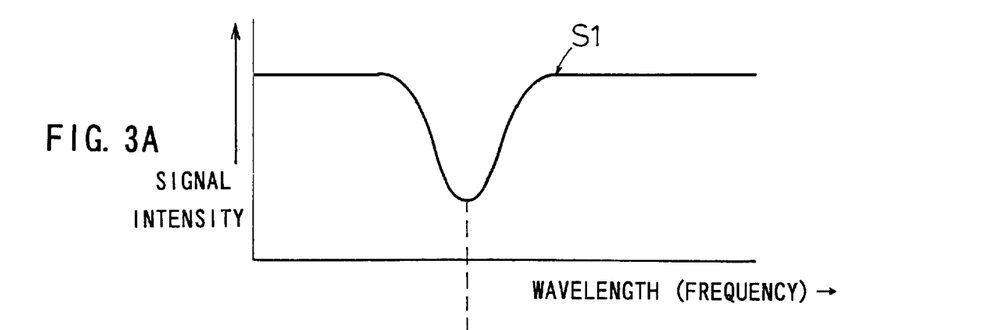
FIGS. 3A through 3D are diagrams illustrative of a process of the carbon isotope analyzing apparatus for detecting a peak value of a 2f signal, FIG. 3A showing an electric signal converted from light detected by a photodetector in the carbon isotope analyzing apparatus shown in FIG. 1, FIG. 3B showing a first derivative signal of the electric signal converted from the light detected by the photodetector, FIG. 3C showing a second derivative signal of the electric signal converted from the light detected by the photodetector, FIG. 3D showing a third derivative signal of the electric signal converted from the light detected by the photodetector.

The oscillator 20 modulates the drive current for the laser diode 13 with the frequency f. Laser light emitted from the laser diode 13 resonates with $^{12}CO_2$ and $^{13}CO_2$ in the specimen cell 2, and is absorbed and detected by the photodetector 14. The laser light detected by the photodetector 14 is converted into an electric signal (also referred to as a "detected light signal") S1 whose waveform is illustrated in FIG. 3A. Thereafter, the electric signal S1 is detected in synchronism with the frequency 2f, which is twice the fundamental frequency f of the oscillator 20, by the lock-amplifier 15. The signal intensity of a 2f spectrum of the light absorption spectrum is measured and detected at an output terminal 31 of the lock-in amplifier 15.

Figure 3B:
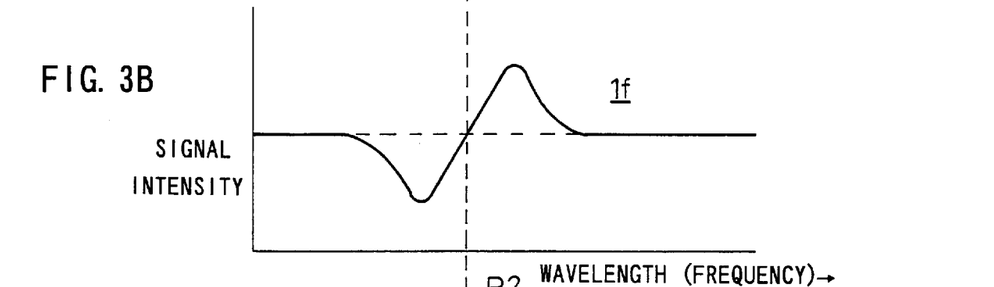
Figure 3C:
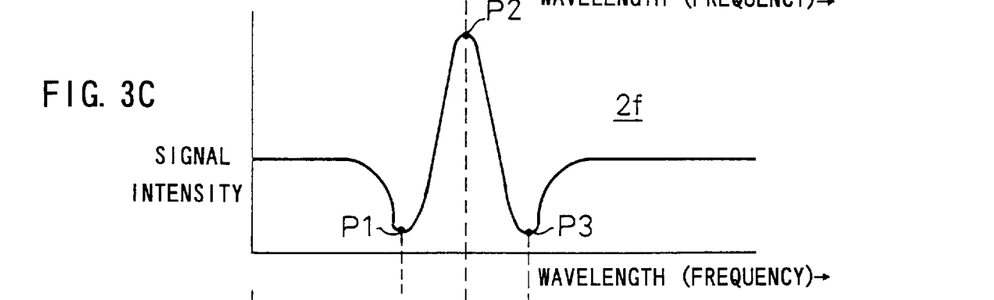

A first derivative signal, i.e., a 1f component (also referred to as a "1f spectrum") of the absorption spectrum, of the detected light signal S1 has a waveform shown in FIG. 3B. A 2f component (also referred to as a "2f spectrum" or a "second derivative signal") of the absorption spectrum that appears at the output terminal 31 of the lock-in amplifier 15 has a waveform shown in FIG. 3C. The lock-in amplifier 16 detects the detected light signal S1 in synchronism with the frequency 3f, which is three times the fundamental frequency f of the oscillator 20, thereby detecting a 3f component (also referred to as a "3f spectrum" or a "third derivative signal") of the absorption spectrum. The 3f component has a waveform shown in FIG. 3D.

Figure 3D:
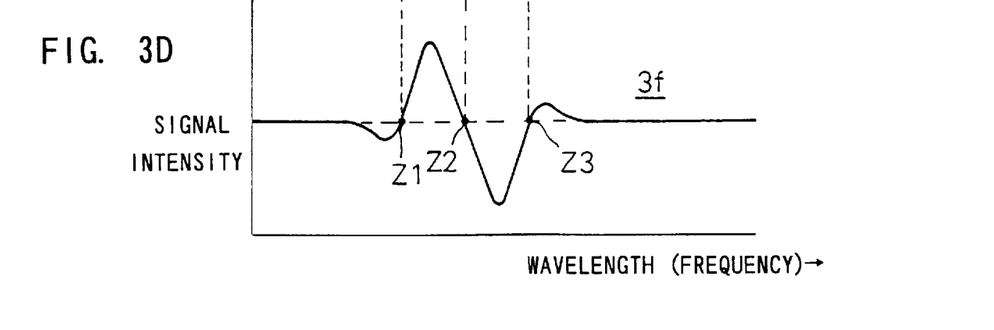

The 3f component shown in FIG. 3D is used as a wavelength discrimination curve. The output signal from the lock-in amplifier 16 is fed back to the drive current for the laser diode 13 through the switches 23, 22, the adder 19, and the current controller 18 in order to Lock the oscillation wavelength of the laser diode 13 to zero-crossing points Z1, Z2, Z3 of the wavelength discrimination curve. The output signal from the lock-in amplifier 16 is inverted in polarity by the inverting amplifier 24. The timing of the feedback process is controlled by controlling the opening and closing of the switch 22. The polarity of the output signal from the lock-in amplifier 16 as a feedback control signal is controlled by controlling the switch 23.

After the switch 22 is opened as shown in FIG. 1 and the switch 23 selects the non-inverted output signal from the lock-in amplifier 16 in response to control signals from the controller 21, the switch 22 is closed by a control signal from the controller 21. At this time, the oscillation wavelength of the laser diode LD is locked to the point "a" in FIG. 8 which corresponds to the point Z1 in FIG. 3D. After the oscillation wavelength is stably locked, the output signal from the lock-in amplifier 15 is sampled several times by the controller 21, which determines an average value of the samples to measure a signal value (signal intensity) at the point "a".

Then, the switch 22 is opened, the switch 23 is shifted to select the inverted signal S2, the controller 21 selects the current value I2 for the drive current, and thereafter the switch 22 is closed. The oscillation wavelength of the laser diode LD is now locked to the point "b" in FIG. 8 which corresponds to the point Z2 in FIG. 3D. The output signal from the lock-in amplifier 15 is sampled several times again by the controller 21, which determines an average value of the samples to measure a signal value (signal intensity) at the point "b".

The controller 21 successively selects the current values I3, I4, I6 for the drive current for measurement at the point "c" in FIG. 8 corresponding to the point Z3 in FIG. 3D, the point "d" in FIG. 8 corresponding to the point Z1 in FIG. 3D, and the point "g" in FIG. 8 corresponding to the point Z3 in FIG. 3D. The controller 21 determines signal values at the respective points "c", "d", "e" in the same manner as described above to determine the signal value at the point "a". For measurement at the point "e" in FIG. 8 corresponding to the point Z2 in FIG. 3D, the controller 21 selects the current value I5 for the drive current, and determines a signal value at the respective point "e" in the same manner as described above to determine the signal value at the point "a".

In this manner, the signal intensities are determined successively at the points "a", "b", "c", "d", "e", "g" in the order named. The absorption intensity of $^{12}CO_2$ is determined from the signal intensities at the points "a", "b", "c", and the absorption intensity of $^{13}CO_2$ is determined from the signal intensities at the points "d", "e", "g". Then, a carbon isotopic abundance ratio is determined from the ratio of these determined absorption intensities. Specifically, if it is assumed that the signal intensities at the respective points "a", "b", "c", "d", "e", "g" are represented by 1a, 1b, 1c, 1d, 1e, 1g and the absorption intensities of $^{12}CO_2$ and $^{13}CO_2$ by X, Y, respectively, then X is calculated according to the equation: X=1b−{(1a+1c)/2}, and Y is calculated according to the equation: Y=1e−{(1d+1g)/2}. The carbon isotopic abundance ratio, indicated by R, is then determined by R=Y/X.

According to another process, the absorption intensities may be determined as the signal values at only two points, i.e., the points "b", "e" in FIG. 8. If this process is employed, however, when the output signal from the lock-in amplifier 15 suffers a DC offset, the absorption intensities contain a measurement error, resulting in an increase in any measurement error of the carbon isotopic abundance ratio. According to the above embodiment of the present invention, since absorption intensities are determined from the peak values at the points "a", "b", "c" and the points "d", "e", "g", any DC offset which may be introduced is canceled out by the calculations, and the problem of an increase in any measurement error of the carbon isotopic abundance ratio occurs.

In the embodiment shown in FIG. 1, the laser diode 13 in the 2 μm band comprises any laser diode having a wavelength range from about 1.9 to 2.1 μm and capable of continuously oscillating at normal temperature.

Since a spectrum with a large light absorption intensity of $CO_2$, particularly a large light absorption intensity of $^{13}CO_2$, is measured using the laser diode 13 in the 2 μm band, the spectrum can be measured with high sensitivity, dispensing with any pretreatment process for concentrating $CO_2$ in an exhalation.

Inasmuch as the absorption intensities of $^{12}CO_2$ and $^{13}CO_2$ are measured at a total of six points, it is possible to determine a carbon isotopic abundance ratio at a high speed, i.e., within a short period of time. The carbon isotope analyzing apparatus according to the embodiment shown in FIG. 1 is capable of determining a carbon isotopic abundance ratio in about 30 seconds. The carbon isotope analyzing apparatus is also highly reliable and small in size because it uses the small and highly reliable laser diode is used as a laser source.

Reasons why the carbon isotope analyzing apparatus provides excellent performance through the use of the laser diode in the 2 μm band will be described below with respect to the topics of A. Selection of LD source, and B. Selection of 2 μm band-LD.

The present invention provides a carbon isotope analyzing apparatus which can analyze carbon isotopes highly accurately at a high speed in clinical locations and which is small in size and inexpensive to manufacture. The carbon isotope analyzing apparatus is based on laser spectrometry. The selection of a laser source for realizing the carbon isotope analyzing apparatus is of prime importance in the determination of the performance and cost of the carbon isotope analyzing apparatus.

A. Selection of LD source:

Variable-wavelength laser sources include a dye laser, a solid-state laser, a laser diode, etc. The dye laser and the solid-state laser are very expensive as they need a pumping laser source such as an argon-gas laser, a high-output laser diode, or the like. They are also disadvantageous in that they cannot carry out high-speed wavelength sweeping and suffer time-consuming measurements as a wavelength selector is controlled for wavelength sweeping. The laser diode does not need any pumping laser source, is small in size and inexpensive to manufacture, and can vary the wavelength at a high speed (within a short period of time) simply by controlling the drive current thereof. Therefore, the laser diode is suitable for use as the laser source in the carbon isotope analyzing apparatus.

B. Selection of 2 μm band-LD:

There are many light absorption spectrums of $CO_2$ in a wavelength range from visible light to infrared radiation. Spectrums of $^{13}CO_2$ that can be used for an isotopic analysis lie in 1.4, 1.6, 2.0, 4.3 μm bands. The light absorption intensity in the 4.3 μm band, among these spectrums, is maximum and suitable for an isotopic analysis. As described above, a laser diode for such use is an infrared laser diode made of a lead salt material, which does not oscillate at normal temperature. Because this laser diode needs to be cooled by liquid helium or liquid nitrogen, an expensive and large freezer is required for cooling the laser diode. Inasmuch as the laser diode of lead salt material oscillates in longitudinal multimodes, it is necessary to select one of the longitudinal multimodes with a diffraction grating or the like, and an optical system is required to select one of the longitudinal multimodes, resulting in a complex apparatus arrangement. At wavelengths longer than 2 μm, inexpensive glass (BK) cannot be used as an optical material for lenses, but expensive zinc selenide is required as a lens material. Furthermore, the photodetector needs to be cooled by liquid nitrogen. As a consequence, the apparatus tends to be large in size and expensive to manufacture.

Laser diodes in the 1.4 and 1.6 μm bands may be made of an InGaAsP material and can oscillate continuously at normal temperature. Therefore, they do not require a freezer for cooling. With these laser diodes, it is possible to use inexpensive glass BK7 as a lens material. Furthermore, a small and inexpensive photodetector such as an InGaAs or Ge photodiode may be used with them. Since these laser diodes do not need to be cooled, they are free of the problems which the laser diode of lead salt suffers. However, $CO_2$ contained in an exhalation to be tested must be concentrated because the light absorption intensity thereof with respect to the laser emission in the above wavelength bands is small.

A laser diode in the 2 μm band can oscillate continuously at normal temperature and hence does not need to be cooled by a freezer. Since the light absorption intensity of $^{13}CO_2$ is large in the 2 μm band, $CO_2$ contained in an exhalation to be tested does not need to be concentrated. The photodetector for use with the laser diode may be an InGaAs photodiode which is small and requires no cooling. Use of the laser diode in the 2 μm band allows an excellent carbon isotope analyzing apparatus to be constructed which cannot be achieved using other laser diodes.

Figure 4:
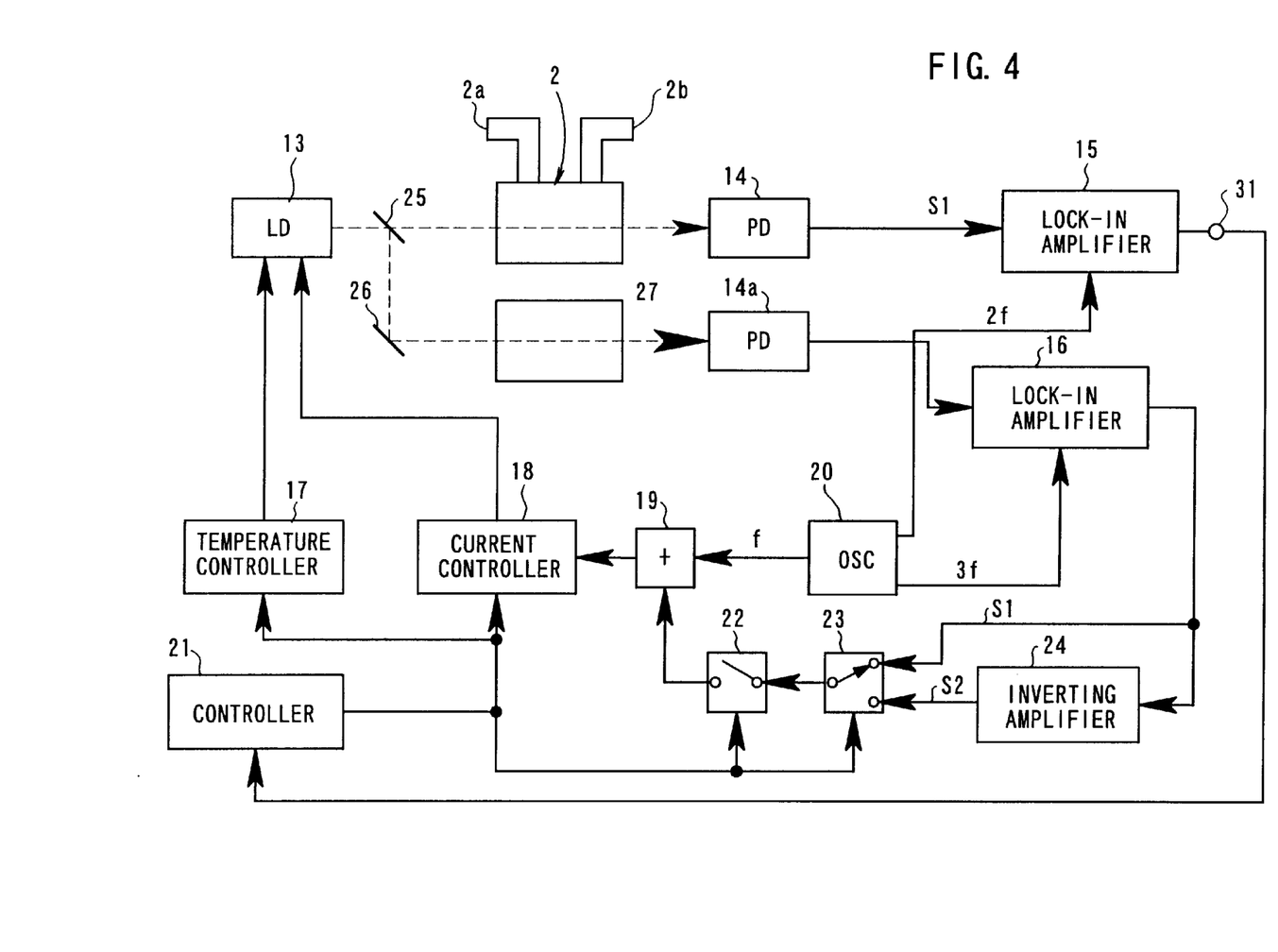
FIG. 4 is a block diagram of a carbon isotope analyzing apparatus according to another embodiment of the present invention.

FIG. 4 shows in block form a carbon isotope analyzing apparatus according to another embodiment of the present invention. The carbon isotope analyzing apparatus shown in FIG. 4 differs from the carbon isotope analyzing apparatus shown in FIG. 1 in that a reference cell 27 is added to lock the wavelength of a laser diode to the absorption spectrum of a gas in the reference cell 27.

As shown in FIG. 4, the carbon isotope analyzing apparatus includes a beam splitter 25, a reflecting mirror 26, the reference cell 27 which sealingly contains a reference gas, and a photodiode 14a. The other elements of the carbon isotope analyzing apparatus shown in FIG. 4 are identical to those of the carbon isotope analyzing apparatus shown in FIG. 1. The reference gas sealed in the reference cell 27 is either a $CO_2$ gas which has a concentration of 100% and contains $^{12}CO_2$ and $^{13}CO_2$ at a naturally occurring ratio or a gas whose composition is the same as a human exhalation.

Laser light emitted from the laser diode 13 is divided into two beams by the laser splitter 25. One of the beams passes through the specimen cell 2 and is then detected by the photodetector 14. The other beam is reflected by the reflecting mirror 26, passes through the reference cell 27, and is then detected by the photodetector 14a. The light detected by the photodetector 14a is converted into an electric signal, which is detected in synchronism with the frequency, which is three times the frequency of the oscillator 20, by the lock-in amplifier 16, for thereby measuring a 3f spectrum of the light absorption spectrum. The oscillation wavelength of the laser diode 13 is locked to the zero-crossing points of the 3f spectrum. Other details of the carbon isotope analyzing apparatus shown in FIG. 4 are the same as the carbon isotope analyzing apparatus shown in FIG. 1. The light absorption intensities of the spectrums are determined by measurements at the six points.

The carbon isotope analyzing apparatus shown in FIG. 4 is capable of controlling the oscillation wavelength of the laser diode 13 without being affected by variations of the components of the gas in the specimen cell 2.

In the embodiments shown in FIGS. 1 and 4, the controller 21 and the current controller 18 function as a means for sweeping the oscillation wavelength of the laser diode 13.

The adder 19, the switches 22, 23, and the inverting amplifier 24 function as a means for locking the oscillation wavelength of the laser diode 13 to the zero-crossing points of the 3f component detected by the lock-in amplifier 16.

Figure 5:
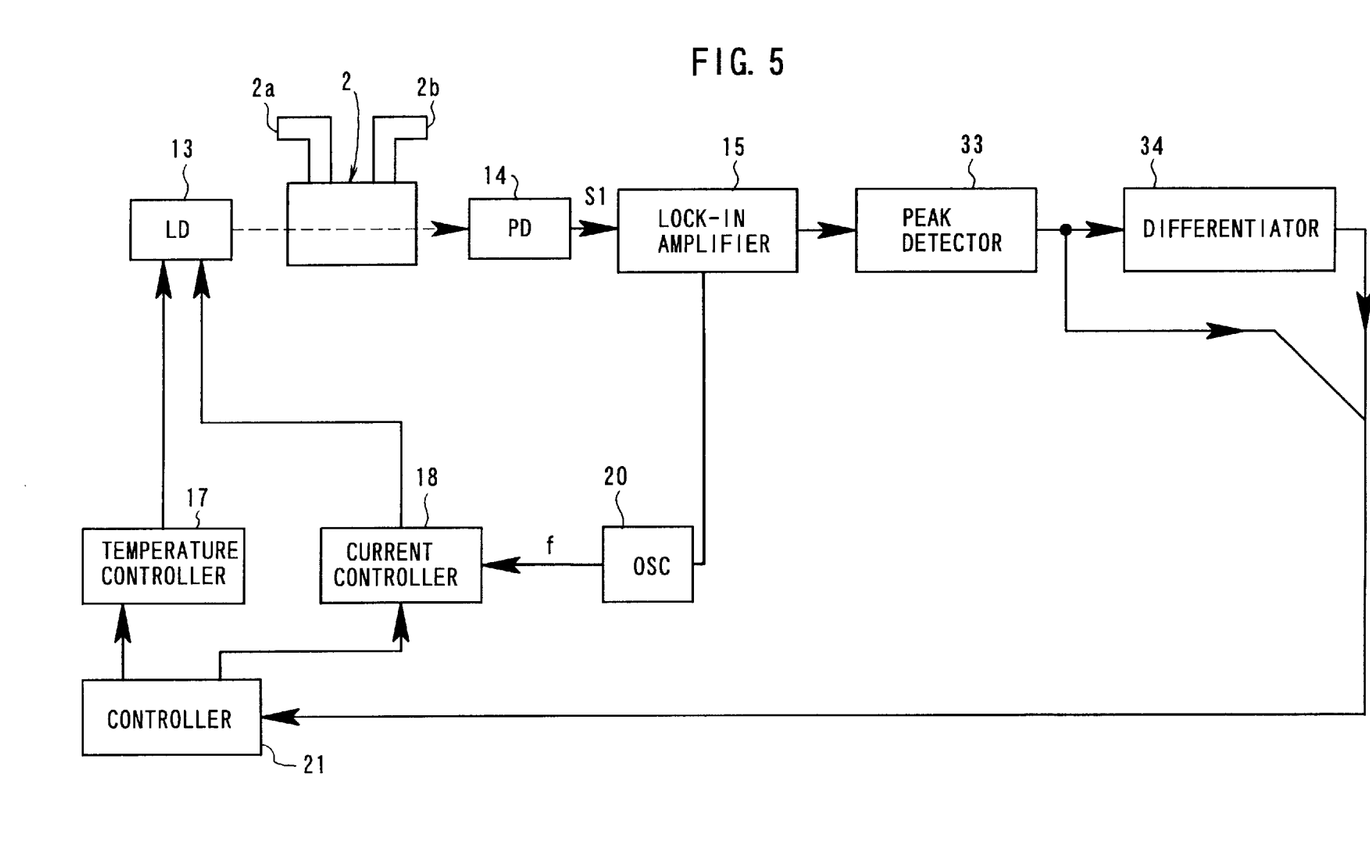
FIG. 5 is a block diagram of a carbon isotope analyzing apparatus according to still another embodiment of the present invention.

FIG. 5 shows in block form a carbon isotope analyzing apparatus according to still another embodiment of the present invention. In the embodiment shown in FIG. 5, the carbon isotope analyzing apparatus is capable of controlling the drive current for the laser diode 13 in the 2 μm band at a high speed to sweep the wavelength at a high speed for measuring a carbon isotopic abundance ratio at a high speed without the need for a pretreatment device, as with the embodiments shown in FIGS. 1 and 4.

As shown in FIG. 5, the carbon isotope analyzing apparatus has a laser diode 13 in the 2 μm band, a specimen cell 2 having a specimen gas inlet 2a and a specimen gas outlet 2b, a photodetector 14, a lock amplifier 15, a laser diode temperature controller 17, an laser diode current controller 18, an oscillator 20 for frequency-modulating a drive current for the laser diode 13, a controller 21 comprising a microcomputer, and a peak detector 33.

The temperature of the laser diode 13 is controlled to establish a sweeping start wavelength by the temperature controller 17 in accordance with a control signal from the controller 21. The laser diode 13 is supplied with a drive current from the current controller 18 in accordance with a control signal from the controller 21. The drive current supplied to the laser diode 13 is controlled by the current controller 18 to enable the laser diode 13 to emit laser light of an appropriate output power. The drive current supplied to the laser diode 13 is also slightly frequency-modulated by a signal having a frequency f which is outputted from the oscillator 20. The drive current supplied to the laser diode 13 is further controlled by the current controller 18 controlled by the controller 21 to sweep the wavelength in the vicinity of the spectrums of $^{12}CO_2$ and $^{13}CO_2$. Laser light emitted from the laser diode 13, which has thus been wavelength-swept and frequency-modulated, is introduced into the specimen cell 2. The introduced laser light acts with the gas in the specimen cell 2, and is absorbed thereby. The light leaving the specimen cell 2 is detected by the photodetector 14, which generates a signal S1 that is applied to the lock-in amplifier 15. The lock-in amplifier 15 then detects a signal in synchronism with a frequency 2f, which is twice the frequency f of the oscillator 20.

The signal thus detected by the lock-in amplifier 15 represents a 2f spectrum of the light absorption spectrum. Based on the output signal from the lock-in amplifier 15, the peak detector 33 detects three peak values of the 2f spectrum. Based on the detected peak values, the controller 21 determines the light absorption intensities of $^{12}CO_2$ and $^{13}CO_2$, and then determines a carbon isotopic abundance ratio from the ratio of the determined light absorption intensities. As a result, the carbon isotope analyzing apparatus shown in FIG. 5 is capable of detecting a signal of high S/N while removing drifts of the intensity of the laser light of the laser diode 13, as with the embodiments shown in FIGS. 1 and 4.

The 2f spectrum measured through the wavelength sweeping by the peak detector 33 may be differentiated by a differentiator 34 to determine a 3f spectrum, and the signal intensities at the zero-crossing points of the 3f spectrum may be determined by the controller 21.

Since the carbon isotope analyzing apparatus shown in FIG. 5 measures a spectrum with a large light absorption intensity of $CO_2$ as with the embodiments shown in FIGS. 1 and 2, it does not require a pretreatment device for concentrating $CO_2$ in an exhalation. The carbon isotope analyzing apparatus shown in FIG. 5 can determine a carbon isotopic abundance ratio at a high speed as it measures the light absorption intensities of $^{12}CO_2$ and $^{13}CO_2$ through current sweeping of the laser diode 13. Since the laser diode 13 is highly reliable, has a long service life, and is small in size, the carbon isotope analyzing apparatus shown in FIG. 5 is highly reliable and has a small size.

With the present invention, as described above, inasmuch as a spectrum with a large light absorption intensity of $^{13}CO_2$ is measured using the laser diode in the 2 $\mu$m band, any pretreatment device for concentrating $CO_2$ is not required.

The carbon isotope analyzing apparatus according to the present invention can quickly analyze carbon isotopes because it measures light absorption intensities at a high speed (in a short period of time).

Since the carbon isotope analyzing apparatus uses a laser diode that is small in size and highly reliable, the carbon isotope analyzing apparatus is small in size and highly reliable, and hence can be used in clinical applications.

Although certain preferred embodiments of the present invention have been shown and described in detail, it should be understood that various changes and modifications may be made therein without departing from the scope of the appended claims.

What is claimed is:

1. An apparatus for determining a carbon isotopic abundance ratio from a light absorption spectrum, comprising:
   a semiconductor laser for emitting laser light having an oscillation wavelength in a 2 $\mu$m band;
   means for sweeping the oscillation wavelength of said semiconductor laser;
   an oscillator for modulating a drive current for said semiconductor laser with a frequency f;
   a specimen cell for containing $CO_2$ therein;
   a photodetector for detecting a light absorption spectrum from the laser light which has been generated by said semiconductor laser and passed through said specimen cell;
   a first lock-in amplifier for detecting a 2f component of said light absorption spectrum;
   a second lock-in amplifier for detecting a 3f component of said light absorption spectrum;
   means for locking the oscillation wavelength of said semiconductor laser to zero-crossing points of the 3f component as detected by said second lock-in amplifier; and
   a controller for determining spectral intensities of $^{12}CO_2$ and $^{13}CO_2$ from peak values at three points of each of said 2f components thereof and determining a carbon isotopic abundance ratio of $^{12}CO_2$ from a ratio of said determined spectral intensities.

2. An apparatus according to claim 1, wherein said 2 $\mu$m band comprises a wavelength range from 1.9 to 2.1 $\mu$m.

3. An apparatus according to claim 1, wherein said controller comprises means for determining said carbon isotopic abundance ratio according to the following formula:

$$[1e-\{(1d+1g)/2\}]/[1b-\{(1a+1c)/2\}]$$

where 1a, 1b, 1c, 1d, 1e, 1g represent the respective peak values of the 2f components of $^{12}CO_2$ and $^{13}CO_2$ at successively higher frequencies.

4. An apparatus for determining a carbon isotopic abundance ratio from a light absorption spectrum, comprising:
   a semiconductor laser for emitting laser light having an oscillation wavelength in a 2 $\mu$m band;
   means for sweeping the oscillation wavelength of said semiconductor laser;
   an oscillator for modulating a drive current for said semiconductor laser with a frequency f;
   a specimen cell for containing $CO_2$ therein;
   a photodetector for detecting a light absorption spectrum from the laser light which has been generated by said semiconductor laser and passed through said specimen cell;
   a first lock-in amplifier for detecting a 2f component of said light absorption spectrum with respect to said specimen cell;
   a reference cell for containing $CO_2$ therein;
   a photodetector for detecting a light absorption spectrum from the laser light which has been generated by said semiconductor laser and passed through said reference cell;
   a second lock-in amplifier for detecting a 3f component of said light absorption spectrum with respect to said reference cell;
   means for locking the oscillation wavelength of said semiconductor laser to zero-crossing points of the 3f component as detected by said second lock-in amplifier; and
   a controller for determining spectral intensities of $^{12}CO_2$ and $^{13}CO_2$ from peak values at three points of each of said 2f components thereof with respect to said specimen cell and determining a carbon isotopic abundance ratio of $^{12}CO_2$ and $^{13}CO_2$ from a ratio of said determined spectral intensities.

5. An apparatus according to claim 4, wherein said 2 $\mu$m band comprises a wavelength range from 1.9 to 2.1 $\mu$m.

6. An apparatus according to claim 4, wherein said controller comprises means for determining said carbon isotopic abundance ratio according to the following formula:

$$[1e-\{(1d+1g)/2\}]/[1b-\{(1a+1c)/2\}]$$

where 1a, 1b, 1c, 1d, 1e, 1g represent the respective peak values of the 2f components of $^{12}CO_2$ and $^{13}CO_2$ at successively higher frequencies.

7. An apparatus for determining a carbon isotopic abundance ratio from a light absorption spectrum, comprising:
   a semiconductor laser for emitting laser light having an oscillation wavelength in a 2 $\mu$m band;
   means for sweeping the oscillation wavelength of said semiconductor laser;
   an oscillator for modulating a drive current for said semiconductor laser with a frequency f;
   a specimen cell for containing $CO_2$ therein;
   a photodetector for detecting a light absorption spectrum from the laser light which has been generated by said semiconductor laser and passed through said specimen cell;
   a lock-in amplifier for detecting a 2f component of said light absorption spectrum;
   means for detecting a peak value of the 2f component detected by said lock-in amplifier; and
   a controller for determining spectral intensities of $^{12}CO_2$ and $^{13}CO_2$ from peak values at three points of each of 2f components thereof and determining a carbon isotopic abundance ratio of $^{12}CO_2$ and $^{13}CO_2$ from a ratio of said determined spectral intensities.

8. An apparatus according to claim 7, wherein said 2 $\mu$m band comprises a wavelength range from 1.9 to 2.1 $\mu$m.

9. An apparatus according to claim 7, wherein said controller comprises means for determining said carbon isotopic abundance ratio according to the following formula:

$$[1e-\{(1d+1g)/2\}]/[1b-\{(1a+1c)/2\}]$$

where 1a, 1b, 1c, 1d, 1e, 1g represent the respective peak values of the 2f components of $^{12}CO_2$ and $^{13}CO_2$ at successively higher frequencies.

10. An apparatus for determining a carbon isotopic abundance ratio from a light absorption spectrum, comprising:

a semiconductor laser for emitting laser light having an oscillation wavelength in a 2 $\mu$m band;

means for sweeping the oscillation wavelength of said semiconductor laser;

an oscillator for modulating a drive current for said semiconductor laser with a frequency f;

a specimen cell for containing $CO_2$ therein;

a photodetector for detecting a light absorption spectrum from the laser light which has been generated by said semiconductor laser and passed through said specimen cell;

a lock-in amplifier for detecting a 2f component of said light absorption spectrum;

means for detecting a peak value of the 2f component detected by said lock-in amplifier;

means for differentiating the 2f component into a 3f component; and a controller for determining three peak values of each of 2f components of $^{12}CO_2$ and $^{13}CO_2$ at zero-crossing points of said 3f component and determining a carbon isotopic abundance ratio of $^{12}CO_2$ and $^{13}CO_2$ from a ratio of determined peak values.

11. An apparatus according to claim 10, wherein said 2 $\mu$m band comprises a wavelength range from 1.9 to 2.1 $\mu$m.

12. An apparatus according to claim 10, wherein said controller comprises means for determining said carbon isotopic abundance ratio according to the following formula:

$$[1e-\{(1d+1g)/2\}]/[1b-\{(1a+1c)/2\}]$$

where 1a, 1b, 1c, 1d, 1e, 1g represent the respective peak values of the 2f components of $^{12}CO_2$ and $^{13}CO_2$ at successively higher frequencies.

13. A method of determining a carbon isotopic abundance ratio from a light absorption spectrum, comprising the steps of:

applying semiconductor laser light modulated with a frequency f and having an oscillation wavelength in a 2 $\mu$m band to a specimen gas containing $^{12}CO_2$ and $^{13}CO_2$;

determining 3f components of each of $^{12}CO_2$ and $^{13}CO_2$ of a light absorption spectrum detected from the laser light which has passed through said specimen gas;

using the determined 3f components as a wavelength discrimination curve and locking said oscillation wavelength to zero-crossing points of said wavelength discrimination curve;

determining three peak values of each of 2f components of $^{12}CO_2$ and $^{13}CO_2$ of said light absorption spectrum; and determining a carbon isotopic abundance ratio of $^{12}CO_2$ and $^{13}CO_2$ from a ratio of determined peak values.

14. A method according to claim 13, wherein said 2 $\mu$m band comprises a wavelength range from 1.9 to 2.1 $\mu$m.

15. A method according to claim 13, wherein said step of determining the carbon isotopic abundance ratio comprises the step of determining said carbon isotopic abundance ratio according to the following formula:

$$[1e-\{(1d+1g)/2\}]/[1b-\{(1a+1c)/2\}]$$

where 1a, 1b, 1c, 1d, 1e, 1g represent the respective peak values of the 2f components of $^{12}CO_2$ and $^{13}CO_2$ at successively higher frequencies.

* * * * *